US00PP29616P3

(12) United States Plant Patent
Rijk

(10) Patent No.: US PP29,616 P3
(45) Date of Patent: Aug. 21, 2018

(54) ***BEGONIA* PLANT NAMED 'FIBEGOSORA'**

(50) Latin Name: *Begonia hybrida*
Varietal Denomination: Fibegosora

(71) Applicant: FIDES B.V., De Lier (NL)

(72) Inventor: Nadine Rijk, De Lier (NL)

(73) Assignee: Dümmer Group B.V., De Lier (NL)

( * ) Notice: Subject to any disclaimer, the term of this patent is extended or adjusted under 35 U.S.C. 154(b) by 36 days.

(21) Appl. No.: 14/999,904

(22) Filed: Jul. 14, 2016

(65) Prior Publication Data

US 2018/0020599 P1 Jan. 18, 2018

(51) Int. Cl.
*A01H 5/02* (2018.01)

(52) U.S. Cl.
USPC ..... Plt./343
CPC ..... *A01H 5/0238* (2013.01)

(58) Field of Classification Search
USPC ..... Plt./343, 347, 344, 349
CPC ..... A01H 5/0238; A01H 5/02; A01H 5/00
See application file for complete search history.

(56) References Cited

PUBLICATIONS

Dummen Orange Annuals 2017 vol. 1 Issu, published on Jun. 27, 2016, retrieved on Oct. 17, 2017, retrieved from the Internet at https://issuu.com/dummenorange/docs/catalog_Ir_annuals_el_salvador_eth, cover page and p. 47 (Year: 2016).*

Plantpeddler 2016 Catalog published on Jul. 5, 2015, retrieved on Oct. 17, 2017, retrieved from the Internet at https://issuu.com/plantpeddlerinc/docs/plantpeddler_2016_catalog, 2 introductory pages, pp. 4, 68-69 and back cover (Year: 2015).*

* cited by examiner

*Primary Examiner* — June Hwu
(74) *Attorney, Agent, or Firm* — C. A. Whealy

(57) ABSTRACT

A new and distinct cultivar of *Begonia* plant named 'Fibegosora', characterized by its upright to spreading and mounded plant habit; relatively compact; freely basal branching habit; dark purple-colored leaves; freely and continuously flowering habit; and double flowers that are bright orange in color.

2 Drawing Sheets

Botanical designation: *Begonia hybrida.*
Cultivar denomination: 'FIBEGOSORA'.

BACKGROUND OF THE INVENTION

The present invention relates to a new and distinct cultivar of *Begonia* plant, botanically known as *Begonia hybrida*, and hereinafter referred to by the name 'Fibegosora'.

The new *Begonia* plant is a product of a planned breeding program conducted by the Inventor in Aalsmeer, The Netherlands. The objective of the breeding program was to develop new freely branching and flowering *Begonia* plants with unique and attractive flower colors.

The new *Begonia* plant originated from a cross-pollination made by the Inventor in 2011 of a proprietary selection of *Begonia hybrida* identified as code number BG-0747, not patented, as the female, or seed, parent and a proprietary selection of *Begonia hybrida* identified as code number BG-0845, not patented, as the male, or pollen, parent. The new *Begonia* plant was discovered and selected by the Inventor as a single flowering plant from within the progeny of the stated cross-pollination in a controlled greenhouse environment in Aalsmeer, The Netherlands in 2011.

Asexual reproduction of the new *Begonia* plant by vegetative tip cuttings in a controlled greenhouse environment in Aalsmeer, The Netherlands since 2011 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Fibegosora'. These characteristics in combination distinguish 'Fibegosora' as a new and distinct *Begonia* plant:

1. Upright to spreading and mounded plant habit; relatively compact.
2. Freely basal branching habit.
3. Dark purple-colored leaves.
4. Freely and continuously flowering habit.
5. Double flowers that are bright orange in color.

Plants of the new *Begonia* can be compared to plants of the proprietary parent selections. Plants of the new *Begonia* differ primarily from plants of the parent selections in uniformity as plants of the new *Begonia* are more uniform than plants of the parent selections. In addition, plants of the new *Begonia* are more freely flowering than plants of the parent selections.

Plants of the new *Begonia* can be compared to plants of *Begonia Elatior* hybrid 'Solenia Orange', disclosed in U.S. Plant Pat. No. 10,550. In side-by-side comparisons, plants of the new *Begonia* differ primarily from plants of 'Solenia Orange' in the following characteristics:

1. Plants of the new *Begonia* are more freely branching than plants of 'Solenia Orange'.
2. Plants of the new *Begonia* have smaller leaves than plants of 'Solenia Orange'.

3. Flowers of plants of the new *Begonia* are more fully double than flowers of plants of 'Solenia Orange'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet is a side perspective view of a typical flowering plant of 'Fibegosora' grown in a container.

The photograph on the second sheet is a close-up view of a typical flowering plant of 'Fibegosora'.

DETAILED BOTANICAL DESCRIPTION

Plants used for the aforementioned photographs and following observations and measurements were grown in 12-cm containers during the summer in a glass-covered greenhouse in Rheinberg, Germany. During the production of the plants, day temperatures ranged from 17° C. to 30° C. and night temperatures ranged from 10° C. to 20° C. Plants were eight weeks old when the photograph and the description were taken. In the following description, color references are made to The Royal Horticultural Society Colour Chart, 2007 Edition, except where general terms of ordinary dictionary significance are used.

Botanical classification: *Begonia hybrida* 'Fibegosora'.

Parentage:

*Female, or seed, parent.*—Proprietary selection of *Begonia hybrida* identified as code number BG-0747, not patented.

*Male, or pollen, parent.*—Proprietary selection of *Begonia hybrida* identified as code number BG-0845, not patented.

Propagation:

*Type.*—By vegetative tip cuttings.

*Time to initiate roots, summer.*—About 18 days at temperatures about 22° C. to 30° C.

*Time to initiate roots, winter.*—About 21 days at temperatures about 22° C. to 30° C.

*Time to produce a rooted young plant, summer.*—About 25 days at temperatures about 22° C. to 30° C.

*Time to produce a rooted young plant, winter.*—About 28 days at temperatures about 20° C. to 25° C.

*Root description.*—Medium in thickness, fibrous; typically whitish grey in color; actual color of the roots is dependent on substrate composition, water quality, fertilizer type and formulation, substrate temperature and physiological age of roots; plants of the new *Begonia* have not been observed to form tubers.

*Rooting habit.*—Moderately freely branching; medium density.

Plant description:

*Plant form and growth habit.*—Upright to spreading and mounded plant habit; relatively compact; pendulous with development; freely basal branching with about nine primary branches; moderately vigorous to vigorous growth habit.

*Plant height.*—About 38 cm.

*Plant width.*—About 36 cm.

*Lateral branch description.*—Length: About 5 cm to 13 cm. Diameter: About 8 mm. Internode length: About 4 cm. Texture: Smooth, glabrous. Color: Close to 195B.

*Leaf description.*—Arrangement: Alternate, simple. Length: About 18 cm. Width: About 11 cm. Shape: Ovate to lanceolate. Apex: Acute. Base: Cordate. Margin: Serrate. Texture, upper and lower surfaces: Smooth, glabrous. Venation pattern: Palmate; reticulate. Color: Developing leaves, upper surface: Close to N92A. Developing leaves, lower surface: Close to 59B. Fully expanded leaves, upper surface: Close to N186A; venation, close to N137C. Fully expanded leaves, lower surface: Close to 59B; venation, close to 137C. Petioles: Length: About 6 cm. Diameter: About 7 mm. Texture, upper and lower surfaces: Smooth, glabrous. Color, upper and lower surfaces: Close to 195B.

Flower description:

*Flowering habit.*—Double flowers arranged in axillary cymes; freely flowering habit with numerous flowers developing per plant; flowers pendulous and face outwardly to downwardly.

*Fragrance.*—None detected.

*Natural flowering season.*—Plants in full flower about eight weeks after planting; long flowering period, in the garden plants flower freely and continuously throughout the summer in Northern Europe and can be flowered year-round in greenhouses.

*Flower longevity.*—Individual flowers last about four weeks on the plant; flowers persistent.

*Number of flowers per inflorescence.*—About three.

*Inflorescence height* (*including peduncle*).—About 7.5 cm.

*Inflorescence diameter.*—About 12 cm.

*Female flower buds.*—Length: About 8 mm. Diameter: About 1.1 cm. Shape: Ovoid. Texture: Smooth, glabrous. Color: Close to N30B.

*Female flowers.*—Diameter: About 6.1 cm. Depth (height): About 3.5 cm.

*Female flower tepals.*—Quantity per flower and arrangement: Typically seven per flower arranged in a single whorl. Length: About 2.4 cm. Width: About 2.5 cm. Shape: Ovate. Apex: Acute. Base: Cordate. Margin: Entire. Texture, upper and lower surfaces: Smooth, glabrous. Color: When opening, upper surface: Close to 33B. When opening, lower surface: Close to 34B. Fully opened, upper surface: Close to 32A; color does not fade with development. Fully opened, lower surface: Close to 34B; color does not fade with development.

*Female flower tepaloids.*—None observed.

*Female flower pedicels.*—Length: About 2 cm. Diameter: About 3 mm. Aspect: About 90° from vertical. Strength: Moderately strong. Texture: Smooth, glabrous. Color: Close to 195B.

*Female flowers reproductive organs.*—Quantity of pistils per flower: Four. Pistil length: About 9 mm. Style length: About 8 mm. Style color: Close to 14C. Stigma shape: Curled. Stigma color: Close to 14A. Ovary color: Close to 14D. Fruits and seeds: Fruit and seed development have not been observed on plants of the new *Begonia*.

*Male flower buds.*—Length: About 8 mm. Diameter: About 1.1 cm. Shape: Ovoid. Texture: Smooth, glabrous. Color: Close to N34A.

*Male flowers.*—Diameter: About 7.4 cm. Depth (height): About 3.4 cm.

*Male flower tepals and tepaloids.*—Quantity per flower and arrangement: Typically about 20 per flower arranged in whorls. Length: About 2.6 cm. Width: About 4 cm. Shape: Ovate. Apex: Acute. Base: Cordate. Margin: Entire. Texture, upper and lower surfaces: Smooth, glabrous. Color: When opening, upper surface: Close to 33B. When opening, lower surface: Close to 34B. Fully opened, upper surface: Close to 32A; color does not fade with development. Fully opened, lower surface: Close to 34B; color does not fade with development.

*Male flower pedicels.*—Length: About 4 cm. Diameter: About 4 mm. Aspect: About 90° from vertical. Strength: Moderately strong. Texture: Smooth, glabrous. Color: Close to 195B.

*Male flowers reproductive organs.*—None observed; all transformed into tepaloids.

Disease & pest resistance: Resistance to pathogens and pests common to *Begonia* plants has not been observed on plants of the new *Begonia.*

Temperature tolerance: Plants of the new *Begonia* have been observed to tolerate temperatures ranging from about 4° C. to about 35° C.

It is claimed:

1. A new and distinct *Begonia* plant named 'Fibegosora' as illustrated and described.

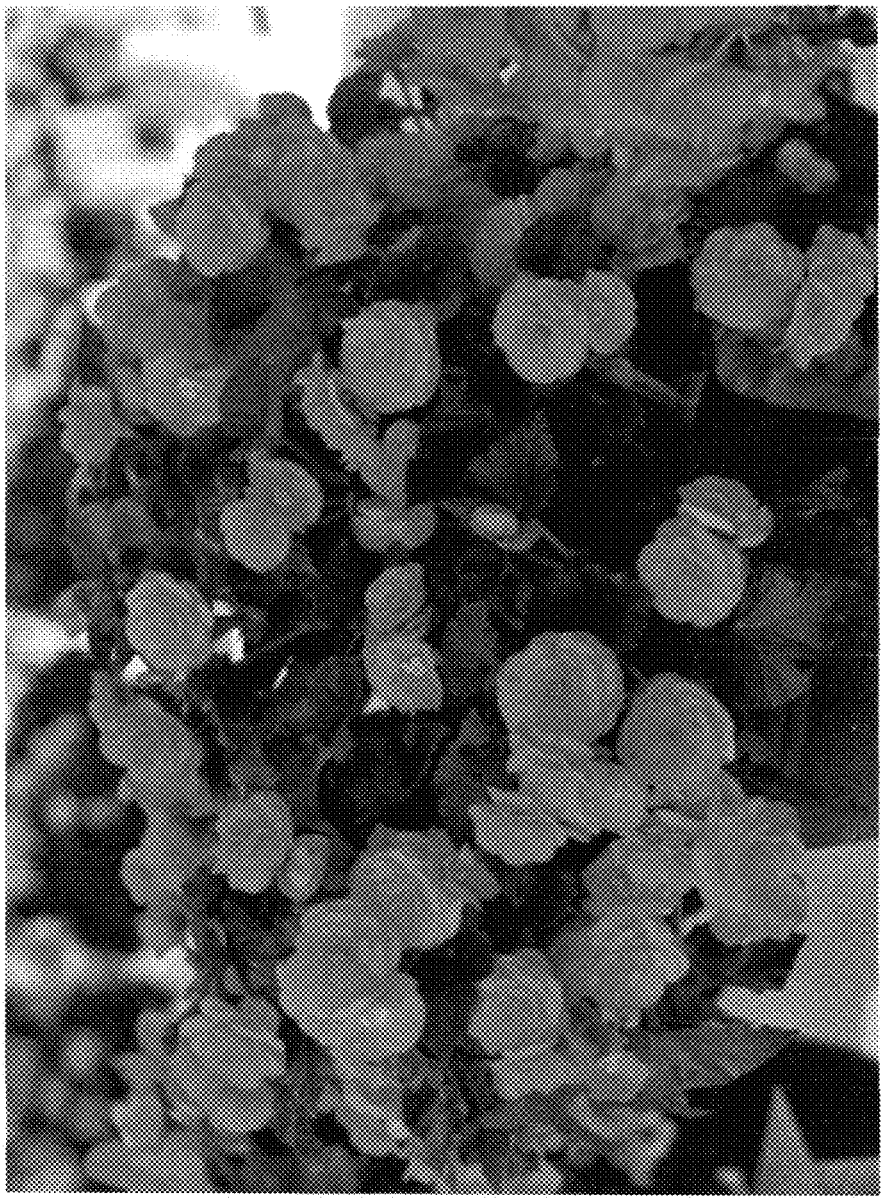

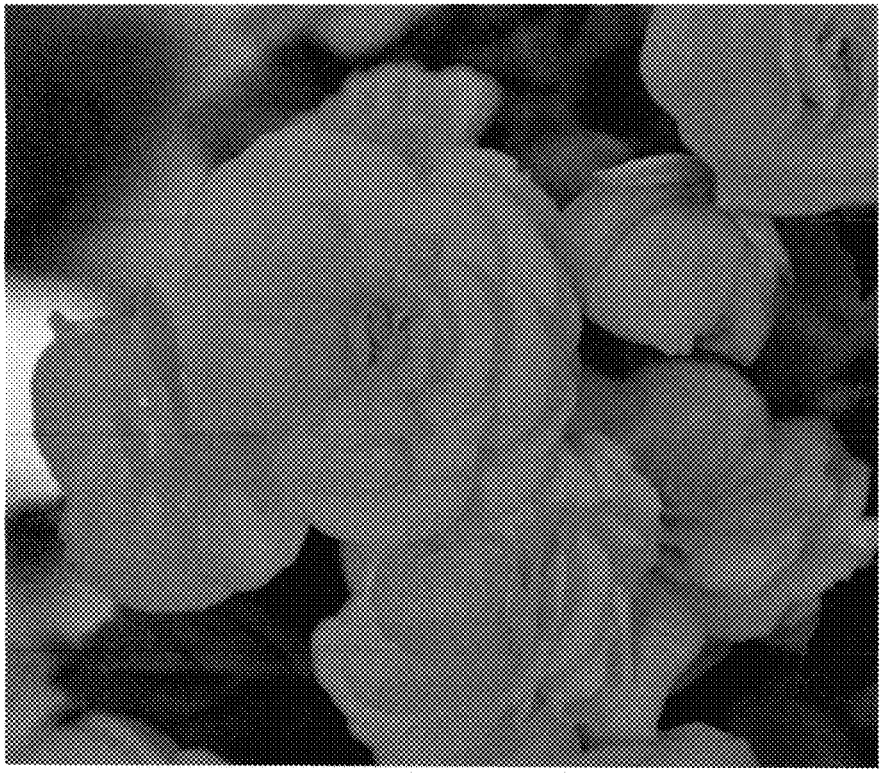

* * * * *